(12) United States Patent
Tseng et al.

(10) Patent No.: US 11,504,400 B2
(45) Date of Patent: Nov. 22, 2022

(54) METHOD OF TREATING MENINGIOMA

(71) Applicant: Da-Tong Ju, Taipei (TW)

(72) Inventors: Hsuan-Ching Tseng, New Taipei (TW); Da-Tong Ju, Taipei (TW); Chi-Tun Tang, Taipei (TW); Chen-Yu Lee, Taipei (TW); Chuang-Hsin Chiu, Taipei (TW); Yan-Chih Liao, Taipei (TW); Hsin-I Ma, New Taipei (TW); Tung-Han Tsai, Kaohsiung (TW)

(73) Assignee: Da-Tong Ju, Taipei (TW)

( * ) Notice: Subject to any disclaimer, the term of this patent is extended or adjusted under 35 U.S.C. 154(b) by 98 days.

(21) Appl. No.: 16/952,116

(22) Filed: Nov. 19, 2020

(65) Prior Publication Data

US 2022/0152122 A1 May 19, 2022

(51) Int. Cl.
| | | |
|---|---|---|
| A61K 35/62 | (2006.01) | |
| A61K 36/756 | (2006.01) | |
| A61K 36/484 | (2006.01) | |
| A61K 36/284 | (2006.01) | |
| A61K 36/282 | (2006.01) | |
| A61K 36/88 | (2006.01) | |
| A61K 36/815 | (2006.01) | |
| A61K 36/539 | (2006.01) | |
| A61K 36/481 | (2006.01) | |
| A61K 36/236 | (2006.01) | |
| A61K 36/65 | (2006.01) | |
| A61K 36/8988 | (2006.01) | |
| A61K 36/06 | (2006.01) | |
| A61K 36/884 | (2006.01) | |
| A61K 36/537 | (2006.01) | |
| A61K 36/16 | (2006.01) | |
| A61K 36/17 | (2006.01) | |
| A61K 36/714 | (2006.01) | |
| A61K 36/54 | (2006.01) | |
| A61K 36/9068 | (2006.01) | |
| A61P 35/00 | (2006.01) | |
| A61K 36/718 | (2006.01) | |

(52) U.S. Cl.
CPC .............. *A61K 35/62* (2013.01); *A61K 36/06* (2013.01); *A61K 36/16* (2013.01); *A61K 36/17* (2013.01); *A61K 36/236* (2013.01); *A61K 36/282* (2013.01); *A61K 36/284* (2013.01); *A61K 36/481* (2013.01); *A61K 36/484* (2013.01); *A61K 36/537* (2013.01); *A61K 36/539* (2013.01); *A61K 36/54* (2013.01); *A61K 36/65* (2013.01); *A61K 36/714* (2013.01); *A61K 36/718* (2013.01); *A61K 36/756* (2013.01); *A61K 36/815* (2013.01); *A61K 36/88* (2013.01); *A61K 36/884* (2013.01); *A61K 36/8988* (2013.01); *A61K 36/9068* (2013.01); *A61P 35/00* (2018.01); *A61K 2236/39* (2013.01)

(58) Field of Classification Search
None
See application file for complete search history.

(56) References Cited

U.S. PATENT DOCUMENTS

2011/0183015 A1* 7/2011 Hsieh ..................... A61K 36/71
424/773

* cited by examiner

*Primary Examiner* — Michael Barker
(74) *Attorney, Agent, or Firm* — Bacon & Thomas, PLLC

(57) ABSTRACT

The present invention relates to a method of treating meningioma including administering a Chinese medicine composition to a subject in need thereof; wherein the Chinese medicine composition is an extract of a first mixture comprising *Coptis chinensis*, *Phellodendron amurense*, *Glycyrrhiza uralensis*, *Atractylodes lancea*, *Artemisia carvifolia*, *Anemarrhena asphodeloides*, and *Cortex Lycii*.

21 Claims, No Drawings

METHOD OF TREATING MENINGIOMA

BACKGROUND OF THE INVENTION

1. Field of the Invention

The present invention relates to a method for treating meningioma.

2. Description of Related Art

Due to the potential of Chinese herbal medicine for treating cancer, traditional Chinese herbal medicine has gradually attracted attention in recent years. The principle of applying Chinese herbal medicine is based on the practice of traditional Chinese medicine theory.

Meningioma is a primary intracranial tumor, which mainly occurs in the area covered by meninges tissue in the brain. It is an extra axial lesion formed by arachnoid cells in the meninges tissue. Most meningiomas grow slowly and are not easily found by patients in the early stages. However, when symptoms are observed, most of the patients' tumors have occupied considerable space in brain. The main symptoms of meningioma are mostly headache, dizziness, vomiting, personality abnormalities, or vision loss caused by increased intracranial pressure.

The current methods for treating meningioma include resection, radiation therapy and chemotherapy, wherein resection is the main one. However, some meningioma cannot be completely removed such that the treatment needs to include radiation therapy or chemotherapy. However, the process of treating meningioma often causes a variety of side effects, leading to the poor quality of life for patients. In addition, the possibility of relapse is very high even though the patient has been treated and recovered. Therefore, there is an urgent need to provide a new method for treating patients with meningioma to alleviate the condition of meningioma patients, improve their quality of life, or prolong their survival time.

SUMMARY OF THE INVENTION

The present invention relates to a composition and method for treating meningioma, which can alleviate meningioma ire patients, improve their quality of life, or prolong their survival time.

The present invention provides a method for treating meningioma, comprising: administering a Chinese medicine composition to a subject in need thereof; wherein the Chinese medicine composition is an extract of a first mixture comprising *Coptis chinensis, Phellodendron amurense, Glycyrrhiza uralensis, Atractylodes lancea, Artemisia carvifolia, Anemarrhena asphodeloides*, and *Cortex lycii*.

The present invention further provides a method for treating meningioma, comprising: administering said Chinese medicine composition to a subject in need thereof. Specifically, an effective amount of said Chinese medicine composition is administered to the subject in need thereof.

The Chinese medicine composition may be prepared by the following steps: providing the first mixture; mixing the first mixture with water to form a second mixture; heating the second mixture to obtain a crude extract; and filtering the crude extract to keep a liquid extract and obtain the Chinese medicine composition.

The first mixture of the present invention may comprise 4-6 parts by weight of *Coptis chinensis*, 4-6 parts by weight of *Phellodendron amurense*, 4-6 parts by weight of *Glycyrrhiza uralensis*, 4-6 parts by weight of *Atractylodes lancets*, 4-6 parts by weight of *Artemisia carvifolia* 4-6 parts by weight of *Anemarrhena asphodeloides*, and 4-6 parts by weight of *Cortex lycii*.

The first mixture of the present invention may further comprise at least one ingredient selected from the group consisting of *Scutellaria baicalensis, Astragalus propinquus, Ligusticum striatum, Paeonia veitchii Gastrodia elata, Poria cocos, Alisma plantago aquatic, Salvia miitiorrhiza, Ginkgo biloba, Ephedra sinica, Aconitum carmichaeli Debx, Cinnamotnum cassia, Zingiber officinale*, and *Pheretima aspergillum*.

The first mixture of the present invention may further comprise at least one ingredient selected from the group consisting of 9-31 parts by weight of *Scutellaria baicalensis*, 14-36 parts by weight of *Astragalus propinquus*, 2-4 parts by weight of *Ligusticum striatum*, 2-4 parts by weight of *Paeonia venchii*, 2-14 parts by weight of *Gastrodia elata*, 3-5 parts by weight of *Poria cocos*, 3-6 parts by weight of *Alisma plantago aquatic*, 2-6 parts by weight of *Salvia miltiorrhiza*, 2-4 parts by weight of *Ginkgo biloba*, 2-4 parts by weight of *Ephedra sinica*, 4-6 parts by weight of *Aconitum carmichaeli Debx*, 4-6 parts by weight of *Cinnamomum cassia*, 4-6 parts by weight of *Zingiber officinale*, and 7-9 parts by weight of *Pheretima aspergillum*.

The first mixture of the present invention may further comprise *Scutellaria baicalensis, Astragalus propinquus, Ligusticum striatum, Paeonia veitchii, Gastrodia elata, Poria cocos, Alisma plantago-aquatic, Salvia miltiorrhiza*, and *Ginkgo biloba*. In one aspect of the present invention, the first mixture may further comprise 9-31 parts by weight of *Scutellaria baicaiensis*, 14-36 parts by weight of *Astragalus propinquus*, 2-4 parts by weight of *Ligusticum striatum*, 2-4 parts by weight of *Paeonia veitchii*, 2-14 parts by weight of *Gastrodia elata*, 3-5 parts by weight of *Poria cocas*, 3-6 parts by weight of *Alisma plantago-aquatic*, 2-6 parts by weight of *Salvia miltiorrhiza*, and 2-4 parts by weight of *Ginkgo biloba*.

The first mixture of the present invention may further comprise *Ephedra sinica*. In one aspect of the present invention, the first mixture may further comprise 2-4 parts by weight of *Ephedra sinica*.

The first mixture of the present invention may further comprise *Aconitum carmichaeli Debx*. In one aspect of the present invention, the first mixture may further comprise 4-6 parts by weight of *Aconitum carmichaeli Debx*.

The first mixture of the present invention may further comprise *Cinnamomum cassia*. In one aspect of the present invention, the first mixture may further comprise 4-6 parts by weight of *Cinnamomum cassia*.

The first mixture of the present invention may further comprise *Zingiber officinale*. In one aspect of the present invention, the first mixture may further comprise 4-6 parts by weight of *Zingiber officinale*.

The first mixture of the present invention may further comprise *Pheretima aspergillum*. In one aspect of the present invention, the first mixture may further comprise 7-9 parts by weight of *Pheretima aspergillum*.

In the present invention, the part by weight of the first mixture may be 2.5-5 gram per part, preferably 3-4 gram per part, more preferably 3.75 gram per part, but the present invention is not limited thereto.

In the present invention, the term "treat" or "treatment" used herein refers to administer a Chinese medicine composition of the present invention to a subject in need thereof, thereby inhibiting, curing, improving, healing, ameliorating, alleviating, changing, or affecting a disease or the tendency of a disease. For instance, the method of the present invention may be used to inhibit the division, replication, proliferation, invasion, or transmigration of meningioma.

In the present invention, the term "effective amount" used herein refers to a necessary dose leading to expected therapeutic effects in a subject treated, and it may be adjusted depending on the route of administration, the use of excipients and the combined use with other medicaments.

The Chinese medicine composition of the present invention may be administered via oral administration or injection.

The Chinese medicine composition of the present invention may further comprise pharmaceutically acceptable carrier, stabilizer, thinner, dispersant, suspending agent, thickener, excipient or the combination thereof.

In the present invention, the term "acceptable" used herein means that it should be compatible with the Chinese medicine composition, preferably be able to stabilize the Chinese medicine composition, and cannot jeopardize the subject treated.

The present invention is not restrictive of the method for decocting Chinese medicine, and it can be implemented in any known manner. The present invention is not restrictive of the method for heating the Chinese medicine, and it can be implemented by any known method, such as direct heating and double-boiling.

DETAILED DESCRIPTION OF THE PREFERRED EMBODIMENT

The following embodiments are meant to explain the implementation of the present invention, they should be construed as descriptive merely, and should not restrict the remaining part of the present invention. The person having ordinary skills in the art can easily understand other advantages and effects of the present invention. The present invention may also be implemented or applied by other different embodiments, and various details in this specification may also be modified and changed according to different viewpoints and applications without departing from the spirit of the invention.

Unless specified otherwise, all technical and scientific terms described in the specification and claims of the present invention are defined as follows. In the present invention, singular terms, "the" or "said" may refer to one or more Objects, unless specified otherwise. In addition, the term "comprise" is an open-ended transition word which does not limit to the items listed. The foregoing paragraphs are only systematic references and should not be construed as limitations for the subject of the invention. Unless specified otherwise, the materials used in the present invention are commercially available and easy to obtain. Possible sources for obtaining the materials are listed below and it is exemplary only.

In the following preparation examples, the part by weight is 3.75 gram per part.

PREPARATION EXAMPLE 1

Provide 5 parts by weight of *Coptis chinensis*, 5 parts by weight of *Phellodendron amurense*, 5 parts by weight of *Glycyrrhiza uralensis*, 5 parts by weight of *Atractylodes lancea*, 5 parts by weight of *Artemisia carvifolia*, 5 parts by weight of *Anemarrhena asphodeloides*, and 5 parts by weight of *Cortex lycii* to form a first mixture-1; mix the first mixture-1 with 1500 parts by weight of water to form a second mixture-1; decoct the second mixture-1 for 1 hour to form about 400 parts by weight of a crude extract; filter the crude extract and collect the filtrate to obtain a Chinese medicine composition 4 of the present preparation example. The effects of inhibiting activation and proliferation of peripheral blood cancer stem cells could be achieved by adding *Coptis chinensis, Phellodendron amurense, Anemarrhena asphodeloides, Artemisia carvifolia*, and *Cortex Lycii*, and the description about such effects of the same ingredients would be omitted hereinafter.

PREPARATION EXAMPLE 2

The first mixture-1 of Preparation Example 1 was further added with 15 parts by weight of *Scutellaria baicalensis*, 15 parts by weight of *Astragalus propinquus*, 3 parts by weight of *Ligusticum striatum*, 3 parts by weight of *Paeonia veitchii*, 3 parts by weight of *Gastrodia elata*, 4 parts by weight of *Poria cocos*, 4 parts by weight of *Alisma plantago-aquatic*, 3 parts by weight of *Salvia miltiorrhiza*, and 3 parts by weight of *Ginkgo biloba* to form a first mixture-2. Then, extract the first mixture-2 in a manner similar to Preparation Example 1 to obtain a Chinese medicine composition-2 of the present preparation example. The effects of benefiting qi and nourishing blood could be achieved by adding *Astragalus propinquus* or *Salvia miltiorrhiza*. Moreover, the effects of inhibiting activation and proliferation of peripheral blood cancer stem cells could be achieved by adding *Scutellaria baicalensis*, and the description about such effects of the same ingredients would be omitted hereinafter.

PREPARATION EXAMPLE 3

The first mixture-2 of Preparation Example 2 was added with 5 parts by weight of *Scutellaria baicalensis* and 5 parts by weight of *Astragalus propinquus* to form a first mixture-3. Then, extract the first mixture-3 in a manner similar to Preparation Example 1 to obtain a Chinese medicine composition-3 of the present preparation example.

PREPARATION EXAMPLE 4

The first mixture-2 of Preparation Example 2 was added with 10 parts by weight of *Scutellaria baicalensis* and 10 parts by weight of *Astragalus propinquus* to form a first mixture-4. Then, extract the first mixture-4 in a manner similar to Preparation Example 1 to obtain a Chinese medicine composition-4 of the present preparation example.

PREPARATION EXAMPLE 5

The first mixture-4 of Preparation Example 4 was added with 5 parts by weight of *Gastrodia elata* and 3 parts by weight of *Ephedra sinica* to form a first mixture-5. Then, extract the first mixture-5 in a manner similar to Preparation Example 1 to obtain a Chinese medicine composition-5 of the present preparation example.

PREPARATION EXAMPLE 6

The first mixture-5 of Preparation Example 5 was added with 1 parts by weight of *Scutellaria baicalensis* and 1 parts by weight of *Alisma plantago-aquatica* to form a first mixture-6. Then, extract the first mixture-6 in a manner similar to Preparation Example 1 to obtain a Chinese medicine composition-6 of the present preparation example.

PREPARATION EXAMPLE 7

The first mix of Preparation Example 2 was added with 15 parts by weight of *Scutellaria baicalensis* to form a first mixture-7. Then, extract the first mixture-7 in a manner similar to Preparation Example 1 to obtain a Chinese medicine composition-7 of the present preparation example.

PREPARATION EXAMPLE 8

The first mixture-5 of Preparation Example 5 was added with 5 parts by weight of *Gastrodia elata* and 5 parts by weight of *Aconitum carmichaeli Debx* to form a first mixture-8. Then, extract the first mixture-8 in a manner similar to Preparation Example 1 to obtain a Chinese medicine composition-8 of the present preparation example.

PREPARATION EXAMPLE 9

The first mixture-5 of Preparation Example 5 was added with 5 parts by weight of *Scutellaria baicalensis* and 5 parts by weight of *Astragalus propinquus*, 4 parts by weight of *Gastrodia elata*, 5 parts by weight of *Aconitum carmichaeli Debx*, 5 parts by weight of *Cinnamomum cassia* to form a first mixture-9. Then, extract the first mixture-9 in a manner similar to Preparation Example 1 to obtain a Chinese medicine composition-9 of the present preparation example.

PREPARATION EXAMPLE 10

The first mixture-2 of Preparation Example 2 was added with 15 parts by weight of *Astragalus propinquus* and 5 parts by weight of *Cinnamomum cassia* to form a first mixture-10. Then, extract the first mixture-10 in a manner similar to Preparation Example 1 to obtain a Chinese medicine composition-10 of the present preparation example.

PREPARATION EXAMPLE 11

The first mixture-5 of Preparation Example 5 was added with 5 parts by weight of *Astragalus propinquus* and 4 parts by weight of *Gastrodia elata*, 5 parts by weight of *Aconitum carmichaeli Debx*, and 5 parts by weight of *Cinnamomum cassia* to form a first mixture-11. Then, extract the first mixture-11 in a manner similar to Preparation Example 1 to obtain a Chinese medicine composition-11 of the present preparation example.

PREPARATION EXAMPLE 12

The first mixture-1 of Preparation Example 1 was added with 10 parts by weight of *Scutellaria baicalensis*, 35 parts by weight of *Astragalus propinquus*, 3 parts by weight of *Ligusticum striatum*, 3 parts by weight of *Paeonia veitchii*, 3 parts by weight of *Gastrodia elata*, 4 parts by weight of *Poria cocos*, 4 parts by weight of *Alisma plantago-aquatic*, 3 parts by weight of *Salvia miltiorrhiza*, and 3 parts by weight of *Ginkgo biloba* to form a first mixture-12. Then, extract the first mixture-12 in a manner similar to Preparation Example 1 to obtain a Chinese medicine composition-12 of the present preparation example.

PREPARATION EXAMPLE 13

The first mixture-3 of Preparation Example 3 was added with 10 parts by weight of *Astragalus propinquus*, 2 parts by weight of *Gastrodia elata*, 2 parts by weight of *Salvia miltiorrhiza*, 3 parts by weight of *Ephedra sinica*, 5 parts by weight of *Aconitum carmichaeli Debx*, and 5 parts by weight of *Zingiber officinale* to form a first mixture-13. Then, extract the first mixture-13 in a manner similar to Preparation Example 1 to obtain a Chinese medicine composition-13 of the present preparation example. The addition of *Aconitum carmichaeli Debx* or *Zingiber officinale* could be in favor of the brain circulation, assist the repair and regeneration of brain cells or nerve cells, avoid brain cell apoptosis, and improve neurological complications. The description about such effects of the same ingredients would be omitted hereinafter.

PREPARATION EXAMPLE 14

The first mixture-2 of Preparation Example 2 was added with 15 parts by weight of *Astragalus propinquus* and 8 parts by weight of *Pheretima aspergillum* to form a first mixture-14. Then, extract the first mixture-14 in a manner similar to Preparation Example 1 to obtain a Chinese medicine composition-14 of the present preparation example.

PREPARATION EXAMPLE 15

The first mixture-2 of Preparation Example 2 was added with 15 parts by weight of *Astragalus propinquus* to form a first mixture-15. Then, extract the first mixture-15 in a manner similar to Preparation Example 1 to obtain a Chinese medicine composition-15 of the present preparation example.

EXAMPLE 1

The patient of Example 1 was a patient with meningioma. The microscopic resection guided by neuronavigation was performed on the patient after receiving general anesthesia. After the operation, the patient had ptosis and could not open eyes voluntarily.

A treatment applied to the patient of Example 1 was described below. From day 1, a daily dose of the Chinese medicine composition-2 was administered to the patient every day, wherein the daily dose of the Chinese medicine composition-2 was divided into aliquots for ter in die administration. A follow-up report indicated that the patient still took the medicine as of the reporting date, and the meningioma was gradually shrinking.

EXAMPLE 2

The patient of Example 2 was a patient with meningioma. The microscopic resection guided by neuronavigation was performed on the patient after receiving general anesthesia. Moreover, the patient took Oxiracetam Capsules after discharge.

A treatment applied to the patient of Example 2 was described below, From day 1, a daily dose of the Chinese medicine composition-3 was administered to the patient every day, wherein the daily dose of the Chinese medicine composition-3 was divided into aliquots for ter in die administration. A follow-up report indicated that the patient still took the medicine as of the reporting date, and the meningioma was significantly shrinking.

EXAMPLE 3

The patient of Example 3 was a patient with left petroclival meningioma. The microscopic resection guided by neuronavigation was performed on the patient after receiving general anesthesia. Moreover, the patient took Oxiracetam Capsules and Depakine after discharge.

A treatment applied to the patient of Example 3 was described below. From day 1, a daily dose of the Chinese medicine composition-4 was administered to the patient every day, wherein the daily dose of the Chinese medicine composition-4 was divided into aliquots for ter in die administration. A follow-up report indicated that the patient still took the medicine as of the reporting date, and the meningioma was alleviated completely.

EXAMPLE 4

The patient of Example 4 was a patient with meningioma. The patient was treated with Cyberknife with dose of 5 Gy for 5 consecutive days. A treatment applied to the patient of Example 4 was described below. From day 1, a daily dose of the Chinese medicine composition-5 vas administered to the patient every day, wherein the daily dose of the Chinese medicine composition-5 was divided into aliquots for ter in die administration. A follow-up report indicated that the patient still took the medicine as of the reporting date, and the meningioma was alleviated completely.

EXAMPLE 5

The patient of Example 5 was a patient with left petroclival meningioma and had repeated episodes of headache accompanied by blurred vision. The patient was treated with Cyberknife with dose of 5 Gy for 5 consecutive days. Afterwards, the steroid was administered to the patient. However, the patient's eyelids were still asymmetrical and were unable to open and close normally.

A treatment applied to the patient of Example 5 was described below. From day 1, a daily dose of the Chinese medicine composition-6 was administered to the patient every day, wherein the daily dose of the Chinese medicine composition-6 was divided into aliquots for ter in die administration. A follow-up report indicated that the patient still took the medicine as of the reporting date, the meningioma was alleviated completely, the eyelids were symmetrical, but the left eyelid could not be lifted.

EXAMPLE 6

The patient of Example 6 was a patient with meningioma, having dizziness. The microscopic resection guided by neuronavigation was performed on the patient after receiving general anesthesia. Moreover, the patient took Oxiracetam Capsules and Depakine after discharge. Six months after the operation, the patient was treated with Cyberknife with dose of 5 Gy for 5 consecutive days.

A treatment applied to the patient of Example 6 was described below. From day 1, a daily dose of the Chinese medicine composition-7 was administered to the patient every day, wherein the daily dose of the Chinese medicine composition-7 was divided into aliquots for ter in die administration. A follow-up report indicated that the patient still took the medicine as of the reporting date, the meningioma was alleviated completely, and the cavity left by the tumor was rarely found.

EXAMPLE 7

The patient of Example 7 was a patient with meningioma, having dizziness and repeated episodes of headache accompanied by blurred vision. The microscopic resection guided by neuronavigation was performed on the patient after receiving general anesthesia. Moreover, the patient took Oxiracetam Capsules and Depakine after discharge. Six months after the operation, the patient was treated with Cyberknife with dose of 5 Gy for 5 consecutive days. Afterwards, the steroid was administered to the patient.

A treatment applied to the patient of Example 7 was described below. From day 1, a daily dose of the Chinese medicine composition-8 was administered to the patient every day, wherein the daily dose of the Chinese medicine composition-8 was divided into aliquots for ter in die administration. A follow-up report indicated that the patient still took the medicine as of the reporting date, and the meningioma was alleviated completely.

EXAMPLE 8

The patient of Example 8 was a patient with meningioma, having dizziness and repeated episodes of headache accompanied by blurred vision. The microscopic resection guided by neuronavigation was performed on the patient after receiving general anesthesia. Moreover, the patient took Oxiracetam Capsules and Depakine after discharge. Six months after the operation, the patient was treated with Cyberknife with dose of 5 Gy for 5 consecutive days. Afterwards, the steroid was administered to the patient.

A treatment applied to the patient of Example 8 was described below. From day 1, a daily dose of the Chinese medicine composition-9 was administered to the patient every day, wherein the daily dose of the Chinese medicine composition-9 was divided into aliquots for ter in die administration. A follow-up report indicated that the patient still took the medicine as of the reporting date, and the meningioma was alleviated completely.

EXAMPLE 9

The patient of Example 9 was a patient with meningioma, having dizziness and repeated episodes of headache accompanied by blurred vision. The microscopic resection guided by neuronavigation was performed on the patient after receiving general anesthesia. Moreover, the patient took Oxiracetam Capsules and Depakine after discharge. Six months after the operation, the patient was treated with Cyberknife with dose of 5 Gy for 5 consecutive days. Afterwards, the steroid was administered to the patient.

A treatment applied to the patient of Example 9 was described below. From day 1, a daily dose of the Chinese medicine composition-10 was administered to the patient every clay, wherein the daily dose of the Chinese medicine composition-10 was divided into aliquots for ter in die administration. A follow-up report indicated that the patient still took the medicine as of the reporting date, and the meningioma was alleviated completely without proliferation.

EXAMPLE 10

The patient of Example 10 was a patient with meningioma, having dizziness and repeated episodes of headache accompanied by blurred vision. The microscopic resection guided by neuronavigation was performed on the patient after receiving general anesthesia. Moreover, the patient took Oxiracetam Capsules and Depakine after discharge. Six months after the operation, the patient was treated with Cyberknife with dose of 5 Gy for 5 consecutive days.

Afterwards, the steroid was administered to the patient. After the microscopic resection and Cyberknife were performed on the patient, the patient's left eyelid was unable to open and close normally.

A treatment applied to the patient of Example 10 was described below. From day 1, a daily dose of the Chinese medicine composition-11 was administered to the patient every day, wherein the daily dose of the Chinese medicine composition-11 was divided into aliquots for ter in die administration. A follow-up report indicated that the patient still took the medicine as of the reporting date, the meningioma was alleviated completely, and the patient's left eyelid was able to beat slightly.

EXAMPLE 11

The patient of Example 11 was a patient with meningioma, having dizziness and repeated episodes of headache accompanied by blurred vision. The microscopic resection guided by neuronavigation was performed on the patient after receiving general anesthesia. Moreover, the patient took Oxiracetam Capsules and Depakine after discharge. Six months after the operation, the patient was treated with Cyberknife with dose of 5 Gy for 5 consecutive days.

A treatment applied to the patient of Example 11 was described below. From day 1, a daily dose of the Chinese medicine composition-12 was administered to the patient every day, wherein the daily dose of the Chinese medicine composition-12 was divided into aliquots for ter in die administration. A follow-up report indicated that the patient still took the medicine as of the reporting date, and the meningioma was alleviated completely.

EXAMPLE 12

The patient of Example 12 was a patient with meningioma, having dizziness and repeated episodes of headache accompanied by blurred vision. The microscopic resection guided by neuronavigation was performed on the patient after receiving general anesthesia. Moreover, the patient took Oxiracetam Capsules and Depakine after discharge. Six months after the operation, the patient was treated with Cyberknife with dose of 5 Gy for 5 consecutive days. Afterwards, the steroid was administered to the patient. After the microscopic resection and Cyberknife were performed on the patient, the patient's left eyelid was unable to open and close normally.

A treatment applied to the patient of Example 12 was described below. From day 1, a daily dose of the Chinese medicine composition-13 was administered to the patient every day, wherein the daily dose of the Chinese medicine composition-13 was divided into aliquots for ter in die administration. A follow-up report indicated that the patient still took the medicine as of the repotting date, the meningioma was alleviated completely, and the patient was able to close eyes normally.

EXAMPLE 13

The patient of Example 13 was a patient with meningioma, having dizziness and repeated episodes of headache accompanied by blurred vision. The microscopic resection guided by neuronavigation was performed on the patient after receiving general anesthesia. Moreover, the patient took Oxiracetam Capsules and Depakine after discharge. Six months after the operation, the patient was treated with Cyberknife with dose of 5 Gy for 5 consecutive days, Afterwards, the steroid was administered to the patient. After the microscopic resection and Cyberknife were performed on the patient, the patient's left eyelid was unable to open and close normally.

A treatment applied to the patient of Example 13 was described below. From day 1, a daily dose of the Chinese medicine composition-14 was administered to the patient every day, wherein the daily dose of the Chinese medicine composition-14 was divided into aliquots for ter in die administration. A follow-up report indicated that the patient still took the medicine as of the reporting date, the meningioma was alleviated completely, and the left eyelid was able to beat slightly.

EXAMPLE 14

The patient of Example 14 was a patient with meningioma, having dizziness and repeated episodes of headache accompanied by blurred vision. The microscopic resection guided by neuronavigation was performed on the patient after receiving general anesthesia. Moreover, the patient took Oxiracetam Capsules and Depakine after discharge. Six months after the operation, the patient was treated with Cyberknife with dose of 5 Gy for 5 consecutive days, Afterwards, the steroid was administered to the patient.

A treatment applied to the patient of Example 14 was described below. From day 1, a daily dose of the Chinese medicine composition-15 was administered to the patient every day, wherein the daily dose of the Chinese medicine composition-15 was divided into aliquots for ter in die administration. A follow-up report indicated that the patient still took the medicine as of the reporting date, and the meningioma was alleviated completely without proliferation.

Although the present invention has been explained in relation to its preferred embodiment, it is to be understood that many other possible modifications and variations can be made without departing from the spirit and scope of the invention as hereinafter claimed.

What is claimed is:

1. A method for treating meningioma, comprising:
providing a first mixture, wherein the first mixture comprises *Coptis chinensis, Phellodendron amurense, Glycyrrhiza uralensis, Atractylodes lancea, Artemisia* carvifolia, *Anemarrhena asphodeloides*, and *Cortex lycii;*
mixing the first mixture with water to form a second mixture;
heating the second mixture to obtain a crude extract;
filtering the crude extract to keep a liquid extract and obtain a Chinese medicine composition; and
administering the Chinese medicine composition to a subject in need thereof.

2. The method of claim 1, wherein the first mixture comprises 4-6 parts by weight of *Coptis chinensis,* 4-6 parts by weight of *Phellodendron amurense,* 4-6 parts by weight of *Glycyrrhiza uralensis,* 4-6 parts by weight of *Atractylodes lancea,* 4-6 parts by weight of *Artemisia* carvifolia, 4-6 parts by weight of *Anemarrhena asphodeloides*, and 4-6 parts by weight of *Cortex lycii.*

3. The method of claim 2, wherein the part by weight of the first mixture is 2.5-5 gram per part.

4. The method of claim 1, wherein the first mixture further comprises at least one ingredient selected from the group consisting of *Scutellaria baicalensis, Astragalus propinquus, Ligusticum striatum, Paeonia veitchii, Gastrodia elata, Poria cocos, Alisma plantago—aquatic, Salvia* miltiorrhiza, *Ginkgo biloba, Ephedra sinica, Aconitum carmichaeli* Debx, *Cinnamomum cassia, Zingiber officinale*, and *Pheretima aspergillum*.

5. The method of claim 4, wherein the first mixture further comprises at least one ingredient selected from the group consisting of 9-31 parts by weight of *Scutellaria baicalensis*, 14-36 parts by weight of *Astragalus propinquus*, 2-4 parts by weight of *Ligusticum* striatum, 2-4 parts by weight of *Paeonia veitchii*, 2-14 parts by weight of *Gastrodia elata*, 3-5 parts by weight of *Poria cocos*, 3-6 parts by weight of *Alisma plantago—aquatic*, 2-6 parts by weight of *Salvia* miltiorrhiza, 2-4 parts by weight of *Ginkgo biloba*, 2-4 parts by weight of *Ephedra sinica*, 4-6 parts by weight of *Aconitum carmichaeli* Debx, 4-6 parts by weight of *Cinnamomum cassia*, 4-6 parts by weight of *Zingiber officinale*, and 7-9 parts by weight of *Pheretima aspergillum*.

6. The method of claim 5, wherein the part by weight of the first mixture is 2.5-5 gram per part.

7. The method of claim 1, wherein the first mixture further comprises *Scutellaria baicalensis, Astragalus propinquus, Ligusticum striatum, Paeonia veitchii, Gastrodia elata, Poria cocos, Alisma plantago—aquatic, Salvia* miltiorrhiza, and *Ginkgo biloba*.

8. The method of claim 7, wherein the first mixture further comprises *Ephedra sinica*.

9. The method of claim 8, wherein the first mixture further comprises *Aconitum carmichaeli* Debx.

10. The method of claim 7, wherein the first mixture further comprises *Cinnamomum cassia*.

11. The method of claim 9, wherein the first mixture further comprises *Cinnamomum cassia*.

12. The method of claim 9, wherein the first mixture further comprises *Zingiber officinale*.

13. The method of claim 7, wherein the first mixture further comprises *Pheretima aspergillum*.

14. The method of claim 2, wherein the first mixture further comprises
9-31 parts by weight of *Scutellaria baicalensis*, 14-36 parts by weight of *Astragalus propinquus*, 2-4 parts by weight of *Ligusticum* striatum, 2-4 parts by weight of *Paeonia veitchii*, 2-14 parts by weight of *Gastrodia elata*, 3-5 parts by weight of *Poria cocos*, 3-6 parts by weight of *Alisma plantago—aquatic*, 2-6 parts by weight of *Salvia* miltiorrhiza, and 2-4 parts by weight of *Ginkgo biloba*.

15. The method of claim 14, wherein the first mixture further comprises 2-4 parts by weight of *Ephedra sinica*.

16. The method of claim 15, wherein the first mixture further comprises 4-6 parts by weight of *Aconitum carmichaeli* Debx.

17. The method of claim 14, wherein the first mixture further comprises 4-6 parts by weight of *Cinnamomum cassia*.

18. The method of claim 16, wherein the first mixture further comprises 4-6 parts by weight of *Cinnamomum cassia*.

19. The method of claim 16, wherein the first mixture further comprises 4-6 parts by weight of *Zingiber officinale*.

20. The method of claim 14, wherein the first mixture further comprises 7-9 parts by weight of *Pheretima aspergillum*.

21. A method for inhibiting the division, replication, proliferation, invasion, or transmigration of meningioma, comprising:
providing a first mixture, wherein the first mixture comprises *Coptis chinensis, Phellodendron amurense, Glycyrrhiza uralensis, Atractylodes lancea, Artemisia* carvifolia, *Anemarrhena asphodeloides*, and *Cortex lycii*;
mixing the first mixture with water to form a second mixture;
heating the second mixture to obtain a crude extract;
filtering the crude extract to keep a liquid extract and obtain a Chinese medicine composition; and
administering the Chinese medicine composition to a subject in need thereof.

* * * * *